United States Patent
Rabinovich et al.

(10) Patent No.: US 9,249,423 B2
(45) Date of Patent: Feb. 2, 2016

(54) METHOD OF DE-DIFFERENTIATING AND RE-DIFFERENTIATING SOMATIC CELLS USING RNA

(75) Inventors: Peter M. Rabinovich, Madison, CT (US); Sherman M. Weissman, New Haven, CT (US)

(73) Assignee: Yale University, New Haven, CT (US)

( * ) Notice: Subject to any disclaimer, the term of this patent is extended or adjusted under 35 U.S.C. 154(b) by 145 days.

(21) Appl. No.: 13/019,829

(22) Filed: Feb. 2, 2011

(65) Prior Publication Data

US 2011/0165133 A1    Jul. 7, 2011

Related U.S. Application Data

(63) Continuation-in-part of application No. 12/025,700, filed on Feb. 4, 2008, now Pat. No. 8,859,229.

(60) Provisional application No. 60/899,144, filed on Feb. 2, 2007.

(51) Int. Cl.
| | | |
|---|---|---|
| *C12N 5/00* | (2006.01) | |
| *C12N 5/02* | (2006.01) | |
| *C12N 15/85* | (2006.01) | |
| *A61K 48/00* | (2006.01) | |
| *C12N 5/074* | (2010.01) | |

(52) U.S. Cl.
CPC .............. *C12N 15/85* (2013.01); *A61K 48/005* (2013.01); *C12N 5/0696* (2013.01); *C12N 2501/602* (2013.01); *C12N 2501/603* (2013.01); *C12N 2501/604* (2013.01); *C12N 2501/606* (2013.01); *C12N 2510/00* (2013.01)

(58) Field of Classification Search
CPC ..................................................... A61K 35/12
See application file for complete search history.

(56) References Cited

U.S. PATENT DOCUMENTS

| | | | |
|---|---|---|---|
| 4,394,448 A | 7/1983 | Szoka | |
| 4,619,794 A | 10/1986 | Hauser | |
| 5,256,555 A | 10/1993 | Milburn | |
| 5,807,707 A * | 9/1998 | Andrews et al. | 435/69.1 |
| 5,837,693 A | 11/1998 | German | |
| 2003/0083272 A1* | 5/2003 | Wiederholt et al. | 514/44 |
| 2006/0078994 A1 | 4/2006 | Healey | |
| 2006/0188490 A1 | 8/2006 | Hoerr | |
| 2011/0143436 A1* | 6/2011 | Dahl et al. | 435/377 |

FOREIGN PATENT DOCUMENTS

| | | | |
|---|---|---|---|
| WO | WO 00/18958 | * | 9/1998 |
| WO | 9914346 | | 3/1999 |
| WO | WO 2004/065546 | * | 8/2004 |
| WO | WO 2009077134 A2 | * | 6/2009 |

OTHER PUBLICATIONS

Nienhuis et al., 2006, Molecular Therapy, 13: 1031-1049.*
Hanna et al., 2008, Cell, 133: 250-264.*
Muhlrad RNA, 1999, 5:1299-1307.*
Fuke, Nucl Acids Res, 2008, 36:1037-1049.*
Wahle, Jour Biol Chem, 1995, 270:3800-2808.*
Collas et al. Reproductive BioMedicine Online: 762-770, 2006.*
Djuric and Ellis, 202, Stem Cell Research and Therapy, 2010,1:3. pp. 1-6.*
Plath et al. Nature Reviews, 12: 253-265, 2011.*
Sullivan et al. Reproductive BioMed. Online, 16(1): 41-50, Nov. 2008.*
Yakubov, 2010, Biochem Biophys Res Comm, 2010, 394:189-193.*
Buganim, 2012,Cell, 150:1209-1222.*
Stadtfield, 2008, Cell, 2:230-240.*
Takahashi, 2006;Cell. 126:663-676.*
Maherali, 2008, Cell Stem Cell, 3:595-605.*
Arnaud-Barbe, "Transcription of RNA templates by T7 RNA polymerase", Nuc. Acids Res., 26(15):3550-3554 (1998).
Boczkowski, "Induction of tumor immunity and cytotoxic T lymphocyte responses using dendritic cells transfected with messenger RNA amplified from tumor cells", Cancer Res., 80(4):1028-1034 (2001).
Bahceci, "Immunotherapy of B cell malignancies using transiently redirected cytotoxic T cells", Blood, 110(11)Part 1:808A (2007).
Chamberlin, "New RNA polymerase from *Escherichia coli* infected with bacteriophage T7", Nature, 228(5268):227-231 (1970).
Cheung, "Anti-idiotypic antibody facilitates scFv chimeric immune receptor gene transduction and clonal expansion of human lymphocytes for tumor therapy", Hybridoma and Hybridomics, 22(4):209-218 (2003).
Cougot, "Cap-tabolism", Trends in Biochem. Sci., 29(8):436-444 (2004).
Davanloo, "Cloning and expression of the gene for bacteriophage T7 RNA polymerase", Proc. Natl. Acad. Sci. USA, 81(7):2035-2039 (1984).
Dunn and Studier, "Complete nucleotide sequence of bacteriophage T7 DNA and the locations of T7 genetic elements", J. Mol. Biol., 166(4):477-535 (1983).
Elango, "Optimized transfection of mRNA transcribed from a d(A/T)100 tail-containing vector", Biochem. Biophys. Res. Comm., 330(3), 958-966 (2005).

(Continued)

*Primary Examiner* — Valarie Bertoglio
(74) *Attorney, Agent, or Firm* — Pabst Patent Group LLP

(57) ABSTRACT

RNA prepared by in vitro transcription using a polymerase chain reaction (PCR)-generated template can be introduced into a cell to modulate cell activity. This method is useful in de-differentiating somatic cells to pluripotent, multipotent, or unipotent cells; re-differentiating stem cells into differentiated cells; or reprogramming of somatic cells to modulate cell activities such as metabolism. Cells can also be transfected with inhibitory RNAs, such as small interfering RNA (siRNA) or micro RNA (miRNA), or combinations thereof to induce reprogramming of somatic cells. For example, target cells are isolated from a donor, contacted with one or more RNA's causing the cells to be de-differentiated, re-differentiated, or reprogrammed in vitro, and administered to a patient in need thereof. The resulting cells are useful for treating one or more symptoms of a variety of diseases and disorders, for organ regeneration, and for restoration of the immune system.

15 Claims, No Drawings

(56) References Cited

OTHER PUBLICATIONS

Felgner and Ringold, "Cationic liposome-mediated transfection", Nature, 337(6205):387-388 (1989).

Holtkamp, "Modification of antigen-encoding RNA increases stability, translational efficacy, and T-cell stimulatory capacity of dendritic cells", Blood, 108(13):4009-4017 (2006).

Imai, "Chimeric receptors with 4-1BB signaling capacity provoke potent cytotoxicity against acute lymphoblastic leukemia", Leukemia, 18(4):676-684 (2004).

Imai, "Genetic modification of primary natural killer cells overcomes inhibitory signals and induces specific killing of leukemic cells", Blood, 106(1)376-383 (2005).

Kiyama and Oishi, "In vitro transcription of a poly(dA) x poly(dT)-containing sequence is inhibited by interaction between the template and its transcripts", Nucleic Acids Res., 24 (22):4577-4583 (1996).

Kiyama, "Instability of plasmid DNA maintenance caused by transcription of poly (dT)-containing sequences in *Escherichia coli*", Gene, 150(1):57-61 (1994).

Kotani, "Improved methods of retroviral vector transduction and production for gene therapy", Hum. Gene Ther., 5(1)19-28 (1994).

Kowolik, "CD28 costimulation provided through a CD19-specific chimeric antigen receptor enhances in vivo persistence and antitumor efficacy of adoptively transferred T cells", Cancer Res., 66(22):10995-11004 (2006).

Lee, "Efficient autointegration of avian retrovirus DNA in vitro", J. Virol., 64 (12):5958-5965 (1990).

Liu, "Development and validation of a T7 based linear amplification for genomic DNA", BMC Genomics, 4(1):19 (2003).

MacDonald, "Termination and slippage by bacteriophage T7 RNA polymerase", J. Mol, Biol., 232(4):1030-1047 (1993).

Mackett, "General method for production and selection of infectious vaccinia virus recombinants expressing foreign genes", J. Virol., 49(3):857-864 (1984).

Nacheva and Berzal-Herranz, "Preventing nondesired RNA-primed RNA extension catalyzed by T7 RNA polymerase", Eur. J. Biochem., 270 (7):1458-1465 (2003).

Nair, et al., "Induction of primary carcinoembryonic antigen (CEA)-specific cytoxic T lymphocytes in vitro using human dendritic cells transfected with RNA", Nature Biotechnology, 16(4):364-369 (1998).

Nakano, "Efficient coupled transcription/translation from PCR template by a hollow-fiber membrane bioreactor", Biotechnol. Bioeng., 64(2):194-199 (1999).

Nishikawa, "Nonviral vectors in the new millennium: delivery barriers in gene transfer", Hum. Gene Ther., 12(8):861-870 (2001).

Pestova, "Molecular mechanisms of translation initiation in eukaryotes", Proc. Natl. Acad. Sci., 98(13):7029-7036 (2001).

Rabinovich, "Synthetic messenger RNA as a tool for gene therapy", Human Gene Therapy, 17(10):1027-1035 (2006).

Saeboe-Larssen, "mRNA-based electrotransfection of human dendritic cells and induction of cytotoxic T lymphocyte responses against the telomerase catalytic subunit (hTERT)", J. Imm. Methods, 259(1-2):191-203 (2002).

Saltzman and Desai, "Drug delivery in the BME curricula", Annals of Biomedical Engineering, 34(2):270-275 (2006).

Sasaki, et al., "Translation initiation at the CUU codon is mediated by the internal ribosome entry site of an insect picorna-like virus in vitro", J. of Virology, 73:129-1226 (1999).

Schenborn and Mierendorf, "A novel transcription property of SP6 and T7 RNA polymerases: dependence on template structure", Nuc Acids Res., 13 (17):6223-6236 (1985).

Schultze, "Follicular lymphomas can be induced to present alloantigen efficiently: a conceptual model to improve their tumor immunogenicity", Proc. Natl. Acad. Sci., 92 (18):8200-8204 (1995).

Shiramizu, "Identification of a common clonal human immunodeficiency virus integration site in human immunodeficiency virus-associated lymphomas", Cancer Res., 54(8):2069-2072 (1994).

Spratt, "The lognormal frequency distribution and human cancer", J. Surgical Research, 9(3):151-157 (1969).

Stepinski, "Synthesis and properties of mRNAs containing the novel "anti-reverse" cap analogs 7-methyl(3'-O-methyl)GpppG and 7-methyl (3'-deoxy) GpppG", RNA, 7(10):1486-1495 (2001).

Triana-Alonso, "Self-coded 3'-extension of run-off transcripts produces aberrant products during in vitro transcription with T7 RNA polymerase", J. Biol. Chem., 270(11):6298-6307 (1995).

Vlachakis, et al., "Meis3 synergizes with Pbx4 and Hoxb1b in promoting hindbrain fates in the zebrafish",Development, 128:1299-1312 (2001).

Verma and Somia, "Gene therapy—promises, problems and prospects", Nature, 389(6648):239-242 (1997).

Wolff, "Direct gene transfer into mouse muscle in vivo", Science, 247(4949 Pt 1):1465-1468 (1990).

Yamanaka, "Induction of pluripotent stem cells from mouse fibroblasts by four transcription factors", Cell Prolif., 41(Suppl 1):51-56 (2008).

Yu, "induced pluripotent stem cell lines derived from human somatic cells", Science, 318(5858):1917-1920 (2007).

Yu, "Structural and functional analysis of an mRNP complex that mediates the high stability of human beta-globin mRNA", Molecular and Cellular Biology, 21 (17):5879-5888 (2001).

Warren, et al., "Highly efficient reprogramming to pluripotency and directed differentiation of human cells with synthetic modified mRNA", Cell Stem Cell, 7:618-30 (2010).

* cited by examiner

METHOD OF DE-DIFFERENTIATING AND RE-DIFFERENTIATING SOMATIC CELLS USING RNA

CROSS-REFERENCE TO RELATED APPLICATIONS

This application is a continuation-in-part of U.S. Ser. No. 12/025,700 filed Feb. 4, 2008, which claims benefit of and priority to U.S. Ser. No. 60/899,144 filed on Feb. 2, 2007, both of which are incorporated by reference in their entirety.

STATEMENT REGARDING FEDERALLY SPONSORED RESEARCH OR DEVELOPMENT

This invention was made with government support under Grant No. N01-HV-28186 awarded by the National Institutes of Health. The U.S. government has certain rights in the invention.

FIELD OF THE INVENTION

The present invention is generally in the field of genetic engineering employing RNA-mediated gene delivery.

BACKGROUND OF THE INVENTION

The advent of recombinant DNA technology has led to substantial effort to develop methods to facilitate the transfection and transduction of therapeutic and other nucleic acid-based agents to specific cells and tissues. Known techniques provide for the delivery of such agents with a variety of genes, provided in recombinant expression constructs. These constructs are capable of mediating functionality of the genes once they arrive within a cell. Such developments have been critical to many forms of molecular medicine, specifically gene therapy, whereby a missing or defective gene can be replaced by an exogenous copy of the functional gene.

Introduction of foreign nucleic acid into a cell can be accomplished by different methods. Current methods include viral transduction and non-viral delivery, such as electroporation, lipid dependent, polymer dependent, polypeptide dependent delivery, calcium co-precipitation and transfection with "naked" DNA.

Viral approaches typically use a genetically engineered virus to infect a host cell, thereby "transducing" the cell with an exogenous nucleic acid. Among known viral vectors are recombinant DNA viruses, poxviruses, herpes viruses, adenoviruses, and retroviruses. Such recombinants can carry heterologous genes under the control of promoters or enhancer elements, and are able to cause their expression in vector-infected host cells, as reviewed in Mackett et al., *J. Virol.* 49:3 (1994); Kotani et al., *Hum. Gene Ther.* 5:19-28 (1994). Transgene delivery by DNA viruses carries a risk of mutagenicity due to foreign DNA integration into the cellular genome. The use of RNA viruses as vectors is complicated by their cytotoxicity and the risk of undesirable viral propagation. Introduction of viral vectors can result in inactivation or ectopic activation of cellular genes, thereby causing diseases (Lee et al., *J. Virol.* 64:5958-5965 (1990)) or activation of oncogenes (Shiramizu et al., *Cancer Res.*, 54:2069-2072 (1994)). Furthermore, viral vectors are susceptible to undesirable interactions with the host immune system.

Non-viral methods of gene delivery were initially developed on DNA models and include electroporation, liposomal, polymer, polypeptide dependent delivery and transfection with "naked" DNA. Electroporation utilizes the application of brief, high-voltage electric pulses to a variety of animal and plant cells and leads to the formation disturbances in the plasma membrane (U.S. Pat. No. 4,394,448 to Szoka, Jr., et al. and U.S. Pat. No. 4,619,794 to Hauser). Nucleic acids can enter directly into the cell cytoplasm either through these, or as a consequence of the redistribution of membrane components that accompanies membrane restoration. Liposomal and polypeptide dependent approaches mix the material to be transferred with non-toxic polymers to form particles able to penetrate cells and to deliver nucleic acids into cytoplasm (Felgner and Ringold, *Nature*, 337:387-388 (1989), Saltzman and Desai, *Annals of Biomedical Engineering*, 34, 270-275 (2006). "Naked" DNA transfection approaches involve methods where nucleic acids are administered directly in vivo (Herweijer and Wolff, *Gene Ther.* 10(6):453-8 (2003)).

An alternative procedure for non-viral gene delivery is achieved by transfection of mRNA rather than DNA. In principle, unlike DNA transfection, introducing mRNA can have no permanent effect on the genetic structure of the cell, at least in the absence of rare reverse transcription events. There is limited literature on the application of mRNA transfection approaches (for example, Seaboe-Larssen, et al., *J. Imm. Methods*, 259:191-203 (2002); Boczkowski et al., *Cancer Res.*, 60:1028-1034 (2001); and Elango et al., *Biochem. Biophys. Res. Comm.*, 330, 958-966 (2005)), and little in the way of a systematic comparison of DNA and RNA transfection procedures. Most available literature for mRNA transfection is based on methods that involve labor intensive cloning of the gene of interest in special vectors containing a bacteriophage promoter upstream and polyA/T stretch downstream of the cloning site. Not only is cloning time consuming, but recombinant plasmids containing a stretch of poly(A/T) are often unstable in bacterial cells and prone to spontaneous mutations (Kiyama, et al., *Gene*, 150:1963-1969 (1994)). Furthermore, most mRNAs that are generated from d(A/T)n vectors contain a short sequence of heterologous nucleotides following the poly(A) tail. The influence of these heterologous sequences on translation is unknown (Elango et al., *Biochem. Biophys. Res. Comm.*, 330, 958-966 (2005)). There is therefore a need for a transfection method that circumvents the problems associated with vector-dependent transfection methods.

It is an object of the present invention to provide a more convenient and/or efficient method of mRNA production for transfection of different types of cells, including cells which are not transfectable for DNA.

It is also an object of the present invention to provide a method of mRNA transfection with minimal side effects and high efficiency, which allows transient expression of genes and desirable modification of cell phenotype without causing permanent genetic changes, which avoids risk associated with conventional gene therapy.

It is also an object of the present invention to provide a method of cell transfection with multiple genes wherein the level of each gene expression can be individually controlled.

It is an object of the present invention to provide a method of transfection of primary mammalian cells, including human cells, and use of those cells for treatment of a variety of human diseases including neurological diseases, organ regeneration, and restoration of the immune system.

It is another object of the present invention to provide a method of transient cell modification, which allows fast and safe generation of diverse differentiation, de-differentiation, re-differentiation, or reprogrammed states of cells of different cell types, including diverse stem cells from various tissues such as fibroblasts, hematopoietic, epithelial cells and others.

SUMMARY OF THE INVENTION

A method of mRNA production that involves in vitro transcription of PCR generated templates with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length, for use in transfection, is provided. This RNA can efficiently transfect different kinds of cells. This approach results in increased efficiency (fidelity and productivity) of mRNA synthesis and is less time consuming because it does not require cloning, thereby eliminating the unwanted errors and effects related to RNA made on DNA templates obtained with cloning techniques.

The results of transfection of RNAs obtained using this method demonstrate that RNA transfection can be very effective in cells that are exceedingly difficult to transfect efficiently with DNA constructs. Further, the levels of gene expression following mRNA transfection are consistent from cell to cell and these levels can be controlled over a wide range simply by changing the amount of mRNA that is transfected. Due to the high efficiency of transfection, the cells can be simultaneously transfected with multiple genetic constructs. The method can be used to deliver genes or inhibitory nucleic acids into cells not- or only poorly transfectable for DNA, in vitro and in vivo, and modulate cell activity. The methods can be used to de-differentiate, re-differentiate, or re-program cells. For example, cells can be induced to form induced pluripotent stem (iPS) cells. Cells prepared according the disclosed methods are useful in research, and cell therapy, for example by administering the cells to a subject in need thereof for the treatment of a disease or disorder.

DETAILED DESCRIPTION OF THE INVENTION

I. Definitions

The brief life of an mRNA molecule begins with transcription and ultimately ends in degradation. During its life, an mRNA molecule may be processed, edited, and transported prior to translation. During transcription, RNA polymerase makes a copy of a gene from the DNA to mRNA as needed. Eukaryotic RNA polymerase associates with mRNA processing enzymes during transcription so that processing can proceed quickly after the start of transcription. The short-lived, unprocessed or partially processed, product is termed pre-mRNA; once completely processed, it is termed mature mRNA. Eukaryotic pre-mRNA, however, requires extensive processing.

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

Eukaryotic mRNA that has been processed and transported to the cytoplasm (i.e. mature mRNA) can then be translated by the ribosome. Translation may occur at ribosomes free-floating in the cytoplasm, or directed to the endoplasmic reticulum. After a certain amount of time, the message is degraded by RNases into its component nucleotides. The limited longevity of mRNA enables a cell to alter protein synthesis rapidly in response to its changing needs.

Different mRNAs within the same cell have distinct lifetimes. In bacterial cells, individual mRNAs can survive from seconds to more than an hour; in mammalian cells, mRNA lifetimes range from several minutes to days. The greater the stability of an mRNA, the more protein may be produced from that transcript. The presence of AU-rich motifs in some mammalian mRNAs tends to destabilize those transcripts through the action of cellular proteins that bind these motifs. Rapid mRNA degradation via AU-rich motifs is a critical mechanism for preventing the overproduction of potent cytokines such as tumor necrosis factor (TNF) and granulocyte-macrophage colony stimulating factor (GM-CSF). Base pairing with a small interfering RNA (siRNA) or microRNA (miRNA) can also accelerate mRNA degradation.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., *Proc. Natl. Acad. Sci. USA,* 81:2035-39 (1984), or from another source, binds with high specificity, as described by Chamberlin, et al., *Nature,* 228:227-231 (1970).

As used herein, a poly(A) is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

II. Methods of Making mRNA for Use in Transient Transfection

RNA for transient transfection is produced by in vitro transcription using a polymerase chain reaction (PCR)-generated template.

A. Sources of DNA for PCR

DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism. Genes that can be used as sources of DNA for PCR include genes that encode peptides that are important for regulating cellular differentiation. Preferred genes include transcription factors and mRNA-binding proteins, for example, transcription factors that regulate the self-renewal and/or proliferation of stem cells. In some embodiments, the DNA encodes inhibitory RNAs, such as small interfering RNA (siRNA) or micro RNA (miRNA). For example, the DNA may encode an interfering RNA that prevents expression of an mRNA encoding an allogenic antigen. The DNA may encode an RNA that is a pre-RNA, for example pre-miRNA, or a mature RNA, for example mature miRNA. The DNA may encode an RNA that is a fragment or variant of an RNA that retains the biological activity of the RNA.

B. PCR to Produce Templates for In Vitro Transcription

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

1. Untranslated Regions

Chemical structures with the ability to promote stability and/or translation efficiency may also be used. The RNA preferably has 5' and 3' UTRs. Inclusion of 44 base pairs of 5' UTR into the PCR template enables greater translation efficiency of transcribed RNA, for example green fluorescent protein (GFP), when compared to PCR templates containing only 6 base pairs of 5' UTR. The addition of 113 base pairs of 3' UTR enables greater translation efficiency of transcribed GFP RNA when compared to PCR templates containing only 11 base pairs of 3' UTR. In general, the length of the 3' UTR exceeds 100 nucleotides, and therefore 3' UTR longer then 100 nucleotides is preferred. For example, the 3' UTR sequence is between 100 and 5000 nucleotides. The length of the 5' UTR is not as critical as the length of the 3' UTR and can be shorter. For example, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3'UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences increase the efficiency of translation of some RNA transcripts, but do not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

2. RNA Polymerase Promoter

To enable synthesis of RNA from a DNA template without the need for gene cloning, a promoter of transcription should be attached to the DNA template upstream of the sequence to be transcribed. Bacteriophage RNA polymerase promoter sequences can be attached to the 5' UTR by different genetic engineering methods, such as DNA ligation, or can be added to the forward primer (5') of the sequence that is substantially complementary to the target DNA. When a sequence that functions as a promoter for an RNA polymerase is added to 5' end of the forward primer, the RNA polymerase promoter becomes incorporated into the PCR product upstream of the open reading frame that is to be transcribed. In one preferred embodiment, the promoter is a T7 polymerase promoter. Other useful promoters include, but are not limited to, T3 and SP6 RNA polymerase promoters. Consensus nucleotide sequences for T7, T3 and SP6 promoters are known in the art.

3. Poly(A) Tail and 5' Cap

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, *Nuc Acids Res.*, 13:6223-36 (1985); Nacheva and Berzal-Herranz, *Eur. J. Biochem.*, 270:1485-65 (2003). This could lead to runoff transcript bending followed by template exchange with the second DNA strand or transcription of RNA itself (Triana-Alonso et al., *J. Biol. Chem.*, 270:6298-307 (1995); Dunn and Studier, *J. Mol. Biol.*, 166:477-535 (1983); Arnaud-Barbe et al., *Nuc. Acids Res.*, 26:3550-54 (1998); Macdonald et al., 1993), and then to the aberrant transcription in a reverse direction and accumulation of double stranded RNA, which can inhibit gene expression. DNA linearization itself is not sufficient for correct transcription (Triana-Alonso et al., *J. Biol. Chem.*, 270:6298-307 (1995); Dunn and Studier, *J. Mol. Biol.*, 166:477-535 (1983); Arnaud-Barbe et al., 1998 *Nuc. Acids Res.*, 26:3550-54 (1998); Macdonald et al., *J. Mol. Biol.*, 232:1030-47 (1993); Nakano et al., *Biotechnol. Bioeng.*, 64:194-99 (1999). plasmid DNA linearized downstream of a poly(A/T) stretch of 64-100 nucleotides results in good templates (Saeboe-Larssen et al., *J. Immunol. Meth.*, 259:191-203 (2002); Boczkowski et al., *Cancer Res.*, 60:1028-34 (2000); Elango et al., *Biochem Biophys Res Commun.*, 330:958-966 2005). An endogenous termination signal for T7 RNA polymerase encodes an RNA that can fold into a stem-loop structure followed by a track of uridine residues (Dunn and Studier, *J. Mol. Biol.*, 166:477-535 (1983); Arnaud-Barbe et al., 1998 *Nuc. Acids Res.*, 26:3550-54 (1998)). Even without a hairpin, a track of synthesized uridines can attenuate transcription (Kiyama and Oishi, *Nucleic Acids Res.*, 24:4577-4583 (1996). It was hypothesized that the linearization of plasmid DNA downstream of the poly(A/T) stretch probably formed a type of "dynamic" terminator preventing potential aberrant transcription: a 3' extension of the RNA transcript over a poly(A/T) stretch and transcription in the reverse direction will create a growing termination-like signal—an extended poly(U) stretch and a poly(A/U) hairpin. Based on this presumption, reversed PCR primers are designed with a 3' anchoring sequence downstream of the GFP gene and a 5' 100 base stretch of poly(T).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, typically 50-5000 T, for example a 100 T tail, or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines. The examples below demonstrate that a 100 base pair stretch of poly(A) is sufficient to enable efficient translation of an RNA transcript.

Poly(A) tails of RNAs can be further extended following in vitro transcription with the use of a poly(A) polymerase, such as *E. coli* polyA polymerase (E-PAP). Increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine.

5' caps can also provide stability to RNA molecules. In a preferred embodiment, RNAs include a 5' cap. The 5' cap may, for example, be $m^7G(5')ppp(5')G$, $m^7G(5')ppp(5')A$, $G(5')ppp(5')G$ or $G(5')ppp(5')A$ cap analogs, which are all commercially available. The 5' cap can also be an anti-reverse-cap-analog (ARCA) or any other suitable analog. The 5' cap is provided using techniques known in the art (Cougot, et al., *Trends in Biochem. Sci.*, 29:436-444 (2001); Stepinski, et al., *RNA*, 7:1468-95 (2001); Elango, et al., *Biochim. Biophys. Res. Commun.*, 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

III. Methods of Use

RNA, for example RNA prepared by in vitro transcription using a polymerase chain reaction (PCR)-generated template as described above, can be introduced into a cell to modulate cell activity. This method is particularly useful in de-differentiating somatic cells to unipotent, pluripotent or multipotent cells; re-differentiating stem cells into differentiated cells, or reprogramming of somatic cells to modulate cell activities such as metabolism. Cells can also be transfected with inhibitory RNAs, such as small interfering RNA (siRNA) or micro RNA (miRNA), or combinations thereof to induce reprogramming of somatic cells, for example, by preventing expression of allogenic antigens.

A. Introduction of RNA into Target Cells

RNA can be introduced into target cells using different methods, for instance, commercially available methods which include, but are not limited to, electroporation (Maxcyte System (Maxcyte, Inc.), Amaxa Nucleofector-II (Amaxa Biosystems, Cologne, Germany), ECM 830 (Harvard Instruments, Boston, Mass.) or the Gene Pulser II (BioRad, Denver, Colo.), Multiporator (Eppendorf, Hamburg Germany), cationic liposome mediated transfection (TransIT, MirusBio LLC, Lipofectin, Invitrigen), polymer encapsulation, peptide mediated transfection, or biolistic particle delivery systems such as "gene guns" (see, for example, Nishikawa, et al. *Hum Gene Ther.*, 12(8):861-70 (2001).

B. Applications

The methods and reagents have a wide range of applications in therapy and research. The methods are useful for expressing one or multiple RNAs in different cell populations such as fully differentiated cells, partially differentiated cells, such as multipotent cells and non-differentiated cells, such as pluripotent cells. The RNA construct can be delivered into different types of eukaryotic cells as well as into tissues and whole organisms using transfected cells as carriers or cell-free local or systemic delivery of encapsulated, bound or naked mRNA. The methods can be used for any purpose where a transient expression is required or sufficient. The methods can be applied to modulation of cell activity in basic research and therapy, in the fields of cancer, stem cells, acute and chronic infections, genetic disorders, neurological disorders, and autoimmune diseases, including modulation of the developmental pathways.

1. Cells

Cells suitable for use with the method include, but are not limited to, primary cells and established cell lines, embryonic cells, immune cells, stem cells, and differentiated cells including, but not limited to, cells derived from ectoderm, endoderm, and mesoderm, including fibroblasts, parenchymal cells, hematopoietic cells, and epithelial cells. As used herein, stem cells include unipotent cells, multipotent cells, and pluripotent cells; embryonic stem cells, and adult stem cells such as hematopoietic stem cells, mesenchymal stem cells, epithelial stem cells, and muscle satellite cells. In one embodiment, somatic cells are de-differentiated or reprogrammed. Any suitable somatic cell can be used. Representative somatic cells include fibroblasts, keratinocytes, adipocytes, muscle cells, organ and tissue cells, and various blood cells including, but not limited to, hematopoietic cells including hematopoietic stem cells, and cells that provide short- or long-term hematopoietic engraftment. The most preferred cell types include, but are not limited to, human fibroblasts, keratinocytes and hematopoietic stem cells. The methods are particularly useful for de-differentiating and optionally re-differentiating cells, without permanent alteration of cell genomes.

2. RNAs

RNAs useful in the disclosed method include mRNAs, regulatory RNAs, or small RNAs such as siRNA or miRNA wherein the one or more mRNAs encode polypeptides that function to de-differentiate or reprogram the cell. The efficiency of transfection is high. Typically more than 90% of the transfected cell population will express the introduced RNA. Therefore, it is possible to transfect cells with one or more distinct RNAs. For example, the population of cells can be transfected with one or more distinct mRNAs, one or more distinct siRNAs, one or more distinct miRNAs, or combinations thereof. The population of cells can be transfected with multiple RNAs simultaneously in a single administration, or multiple administrations can be staggered minutes, hours, days, or weeks apart. Transfection of multiple distinct RNAs may be staggered. For example, if it is desirable for a first RNA to be expressed prior to expression of one or more additional RNAs.

The level of expression of the transfected RNA can be manipulated over a wide range by changing the amount of input RNA, making it possible to individually regulate the expression level of each transfected RNA. The effective amount of input RNA is determined based on the desired result. Furthermore, the PCR-based technique of mRNA production facilitates the design of mRNAs with different structures and domain combinations.

RNAs useful in the disclosed methods are known in the art, and will be selected based on the target host cell type as well as the pathway or cellular activity to be manipulated, or the therapeutic application. Constructs useful for de-differentiating cells, for example, converting adult, differentiated somatic cells into stem cells, can be constructed based on known genes, mRNAs, or other nucleotide or protein sequences. See, for example, Yu, et al., *Science*, 318:1917-1920 (2007) and Yamanaka, *Cell Prolif.*, 41:51-56 (2008), which describes induced pluripotent stem (iPS) cells obtained from differentiated primary cells by ectopic expression of combinations of transcription factors such as OCT4, SOX2, NANOG, and LIN28, or OCT3/4, SOX2, KLF4 and c-MYC.

Exemplary genomic, mRNA (cDNA), and protein sequences for OCT4 are known in the art, see, for example, (OCT4) POU5F1 POU class 5 homeobox [*Homo sapiens*] Gene ID: 5460, which provides mRNA (cDNA) sequences Genbank accession no. NM_001173531.1 entitled *Homo sapiens* POU class 5 homeobox 1 (POU5F1), transcript variant 3, mRNA; Genbank accession no. NM_002701.4 entitled *Homo sapiens* POU class 5 homeobox 1 (POU5F1) transcript variant 1, mRNA; and Genbank accession no. NM_203289.4 entitled *Homo sapiens* POU class 5 homeobox 1 (POU5F1), transcript variant 2, mRNA. Exemplary genomic, mRNA (cDNA), and protein sequences for SOX2 are also known in the art, see, for example, SOX2 SRY (sex determining region Y)-box 2 [*Homo sapiens*], Gene ID: 6657, which provides mRNA (cDNA) sequence Genbank Accession no. NM_003106.2 entitled mRNA sequence *Homo sapiens* SRY (sex determining region Y)-box 2 (SOX2), mRNA. Exemplary genomic, mRNA (cDNA), and protein sequences for NANOG are also known in the art, see for example NANOG Nanog homeobox [*Homo sapiens*], Gene ID: 79923, which provides the mRNA (cDNA) sequence Genbank accession no. NM_024865.2 entitled *Homo sapiens* Nanog homeobox (NANOG), mRNA. Exemplary genomic, mRNA (cDNA), and protein sequences for LIN28 are also known in the art, see for example LIN28A homolog A (*C. elegans*) [*Homo sapiens*], Gene ID: 79727, which provides the mRNA (cDNA) sequence Genbank accession no. NM_024674.4 entitled *Homo sapiens* lin-28 homolog A (*C. elegans*) (LIN28A), mRNA. Exemplary genomic, mRNA (cDNA), and protein sequences for KLF4 are known in the art, see, for example, KLF4 Kruppel-like factor 4 (gut) [*Homo sapiens*], Gene ID: 9314, which provides the mRNA (cDNA) sequence Genbank accession no. NM_004235.4 entitled *Homo sapiens* Kruppel-like factor 4 (gut) (KLF4), mRNA. mRNA sequences for MYC are also known in the art, see for example MYC v-myc myelocytomatosis viral oncogene homolog (avian) [*Homo*

*sapiens*], Gene ID: 4609, which provides the mRNA (cDNA) sequence Genbank accession no. NM_002467.4 entitled *Homo sapiens* v-myc myelocytomatosis viral oncogene homolog avian) (MYC), mRNA.

Following transfection with one or more RNAs, the cells can be maintained or expanded in culture. Methods for culturing both transfected and non-transfected cells are known in the art, and may include providing additional reagents or supplements to enhance viability and/or growth, for example, growth factors or a feeder layer of cells.

Although transfection using the disclosed mRNAs is transient, once the cells have been induced to de-differentiate, the de-differentiated cells can be maintained in their induced state using tissue culture conditions that are known in the art. For examples, differentiated somatic cells such as fibroblasts that are induced to de-differentiate into iPS cells can be maintained as iPS cells using methods consistent with culturing undifferentiated iPS cells.

The method can also be widely used for re-differentiating or reprogramming of cells, for example, to produce iPS cells that can be further modulated to form hematopoietic stem cells, mesenchymal stem cells, epithelial stem cells, and muscle satellite cells, or differentiated cells of human tissues, including, but not limited to, red blood cells, white blood cells including lymphocytes, platelets, stromal cells, fat cells, bone cells including osteoclasts, epithelial tissue including skin cells, muscle tissue including smooth muscle, skeletal muscle, and cardiac muscle, vascular tissue including endothelial cells, liver tissue including hepatocytes, and nervous tissue including neurons. Methods of inducing differentiation of iPS cells into various differentiated cells types, including, but not limited to, cardiomyocytes, hematopoietic stem cells, bone cells such as, osteoclasts, hepatocytes, retinal cells, and neurons, are known in the art (Song at al., *Cell Res.*, 19(11): 1233-42 (2009), Lamba at al, *PLoS One,* 5(1):e8763 (2010), Gai et al., *Cell Biol Int.* 200933(11):1184-93 (2009). Grigoriadis et al., *Blood,* 115(14):2769-76 (2010)). Stem cells including, but not limited to, isolated embryonic stem cells, hematopoietic stem cells, and induced pluripotent stem cells can be induced to differentiate by transient transfection with RNAs that induce differentiation. Additionally, or alternatively, cells can be re-differentiated by culturing the cells under cell type-specific conditions. For example, iPS cells can be maintained on CF-1 feeders and subsequently adapted to feeder-free conditions. iPS cells can be induced to form differentiated retinal cells by culturing the cells in the presences of noggin, Dkk-1, and IGF-1 (see for example Lamba at al, *PLoS One,* 5(1):e8763 (2010)).

In some embodiments, cells are re-programmed by transient transfection. For example, mRNA from transcription factors such as FoxP3 can be introduced into lymphocytes to increase the formation of regulatory T cells. FoxP3 (forkhead box P3) is a master regulator of development and function of regulatory T cells. Exemplary genomic, mRNA (cDNA), and protein sequences for FoxP3 are known in the art, see, for example Gene ID: 50943, which provides the mRNA (cDNA) sequences Genbank accession no. NM_014009.3 entitled *Homo sapiens* forkhead box P3 (FOXP3), transcript variant 1, mRNA; and Genbank accession no. Nm_001114377.1 entitled *Homo sapiens* forkhead box P3 (FOXP3), transcript variant 2, mRNA.

3. Therapeutic Applications

The disclosed methods are particularly useful in the field of stem cell therapy. In some embodiments, the methods are applied in the context of personalized therapy, for example, to generate iPS cells for introduction into a subject in need thereof. In vitro de-differentiation, re-differentiation, and/or reprogramming can be applied to a variety of different starting cell types and allows fast and safe generation of cells over a diverse range of de-differentiated or re-differentiated states. As used herein, in vitro de-differentiation, re-differentiation, and reprogramming includes de-differentiation, re-differentiation, and reprogramming of isolated cells ex vivo. For example, target cells are first isolated from a donor using methods known in the art, contacted with one or more RNA's causing the cells to be de-differentiated, re-differentiated, or reprogrammed in vitro (ex vivo), and administered to a patient in need thereof. Sources or cells include, but are not limited to peripheral lymphocytes, fibroblasts, keratinocytes primary cell lines, or cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

In some embodiments the cells are contacted with one or more RNA that reprogram the cells to prevent expression of one or more antigens. For example, the RNA may be an interfering RNA that prevents expression of an mRNA encoding antigens as CTLA-4 or PD-1. This method can be used to prepare universal donor cells. RNAs used to alter the expression of allogenic antigens may be used alone or in combination with RNAs that result in de-differentiation of the target cell.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200 or 1000 orders of magnitude. Once target cells have been isolated, they may be propagated by growing in suitable medium according to established methods known in the art. Established cell lines may also be useful in for the disclosed methods. The cells can be stored frozen before transfection, if necessary.

Next the cells are contacted with one or more RNAs in vitro, for example using a transfection technique known in the art. De-differentiation, re-differentiation, and/or re-programming can be monitored, and the desired cell type, for example iPS cells, can be selected for therapeutic administration.

iPS cells can be monitored and selected by identification of specific antigens, such as Nanog, Sox2, SSEA-3, SSEA-4, TRA-1-60, TRA-1-81, Oct 3/4 and alkaline phosphatase, and purified by different methods including magnetic column separation and flow cytometry.

Following de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of RNA-reprogrammed or dedifferentiated cells stored long-term, for later use. In one embodiment, fibroblasts, keratinocytes or hematopoietic stem cells are isolated from a patient and de-differentiation, and/or re-differentiated and/or reprogrammed in vitro to provide iPS cells for the patient.

The method can also be used to reprogram somatic cells wherein RNAs are introduced into cells in order to modulate their viability. For example, mRNA coding dominant-negative mutant p53 protein can temporarily block p53 function. This mRNA can be introduced into cells to protect them from p53-mediated apoptosis caused by metabolic disturbances during de-differentiation.

In some embodiments, cells are reprogrammed to modulate the immune response. For example, lymphocytes can be reprogrammed into regulatory T cells which can be administered to a patient in need thereof to increase or transfer immune tolerance, especially self-tolerance. The induction or administration of Foxp3 positive T cells may be useful in reducing autoimmune responses such graft rejection, and/or reducing, inhibiting or mitigating one or more symptoms of an autoimmune diseases or disorder such as diabetes, multiple sclerosis, asthma, inflammatory bowel disease, thyroiditis, renal disease, rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

4. Diseases to be Treated

The methods can be used to generate cells which may be useful in the treatment of a variety of diseases and disorders, including, but not limited to, neurodegenerative diseases such as Parkinson's, Alzheimer disease, and multiple sclerosis. The methods are also useful for organ regeneration, and for restoration or supplementation of the immune system. For example, cells at different stages of differentiation such as iPS cells, hematopoietic stem cells, multipotent cells or unipotent cells such as precursor cells, for example, epithelial precursor cells, and others can be administered intravenously or by local surgery. The methods can be used in combination with other conventional methods, such as a prescription medication regime, surgery, hormone therapy, chemotherapy and/or radiotherapy.

C. Kits

In one embodiment, a kit includes RNAs, cells, and a means for transfecting the RNA into the cells. The RNAs can be lyophilized or in solution. Kits may optionally include other materials such as cell culture reagents. In an alternative embodiment, a kit provides re-differentiated, dedifferentiated, or reprogrammed cells prepared according to the disclosed methods, and stored and/or shipped refrigerated or frozen for later use. Cells are typically stored in a solution maintaining viability. Kits containing cells should be stored or shipped using a method consistent with viability such as in a cooler containing dry ice so that cells are maintained below 4° C., and preferably below −20° C.

The kits optionally include one or more of the following: bioactive agents, media, excipients and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. Components of the kit may be packaged individually and can be sterile. The kits are generally provided in a container, e.g., a plastic, cardboard, or metal container suitable for commercial sale. Any of the kits can include instructions for use.

The present invention will be further understood by the following non-limiting examples.

EXAMPLES

Materials and Methods

Cells

Neonatal foreskin keratinocytes and nenotal human foreskin fibroblasts were obtained from the Yale Cell Culture Core Facility. Keratinocytes were cultured in serum-free low calcium medium (Epilife, Invitrogen); fibroblasts were cultured in DMEM medium in 10% heat-inactivated fetal bovine serum (Gibco). For reprogramming with mRNA constructs, keratinocytes were electroporated with mRNA transcripts corresponding to reprogramming factors as described below. For initial experiments mRNA corresponding to each of four transcription factors (OCT4, SOX2, KLF4, c-MYC) were used in a 1:1:1:1 ratio respectively. For experiments using high OCT4 concentrations, the same four factors were used in a 3:1:1:1 ratio. For experiments using the initial four factors plus either NANOG or P53DD, the five mRNA transcripts were present in a ratio of 1:1:1:1:1. After viral infection or electroporation, keratinocytes were grown in fresh serum-free, low calcium medium at 37 C and 5% $CO_2$ for 2 days, after which they were trypsinized and seeded onto multi-well plates containing irradiated mouse fibroblasts. Transfected cells were seeded $2.5 \times 10^6$ cells/$cm^2$ and cultured with ES cell medium (DMEM/F12 containing 20% KOSR (vol/vol), 5-10 ng $ml^{-1}$ bFGF, 1 mM L-Gln, 100 µM nonessential amino acids, 100 M 2-mercaptoethanol, 50 U $ml^{-1}$ penicillin and 50 mg $ml^{-1}$ streptomycin). Neonatal human foreskin fibroblasts were used to confirm the expression of individual mRNA constructs of the various reprogramming factors and were cultured in DMEM with 10% heat inactivated fetal bovine serum. Western blot analysis was used to confirm the expression of individual mRNA constructs of the various reprogramming factors.

PCR

Gene amplification was performed with AccuPrime Pfx DNA polymerase (Invitrogen) according to the manufacturer's protocol. 25 to 30 cycles of PCR were performed in standard 50-µl reaction using 0.1 µg of template DNA. The forward primer contained the T7 RNA promoter and an anchoring sequence in the proximal part of the gene expression cassette. The reverse primer, with anchoring sequence in the distal part of the gene expression cassette, contained a stretch of 100 dT residues. 3-step PCR to delete 4-1BB signaling part of the anti-CD19 CIR was performed by a standard procedure.

RNA Synthesis mRNA constructs based on the Pontelina plumata green fluorescent protein ("GFP") sequence of pmaxGFP plasmid (Amaxa Biosystems) were produced in vitro using T7 RNA polymerase (RNAP). Forward primer contained T7 RNA P promoter and anchoring sequence to the proximal part of the GFP expression cassette. Reverse primer with anchoring sequence to distal part of GFP expression cassette contained a stretch of 100 oligo-dT.

mRNA synthesis was performed with mMESSAGE mMASHINE® kit (Ambion), using the procedure recommended by the manufacturer. One hundred to 200 ng of DNA made by PCR with no further purification was used for the standard 20 μl transcription reaction. The product was treated with *Escherichia coli* poly(A) polymerase (from the same kit) in the presence of 1 mM ATP according to the Ambion polyadenylation protocol. The yield of mRNA was 20 to 60 μg of mRNA per reaction. The final product was treated with DNase I (Ambion) and purified with an Ambion MEGAclear kit or by LiCl precipitation. RNA quality was verified by agarose gel electrophoresis, and RNA was stored at –80° C.

In some cases the product was additionally polyadenylated using the reagent of the same kit. The final product was treated with DNaseI and purified by Ambion MEGAclear kit or by LiCl precipitation.

Transfections

Electroporation was performed using an Amaxa NUCLEOFECTOR™-II (Amaxa Biosystems, Cologne, Germany) in accordance with manufacturer recommendations. All cells were electroporated with use of 30-120 mg/ml mRNA per sample. Cells were used in a concentration of 10-250 million per ml. In this interval of values the efficiency of transfection does not depend on cell density. The efficiency of transfection was determined by FACS 18 hours after transfection. Cell viability was determined by trypan blue exclusion.

Cells were used in a concentration of 10-50 million per ml. In this interval of values the efficiency of transfection does not depend on cell density. The efficiency of transfection was determined by FACS eighteen hours after transfection. Cell viability was determined by trypan blue exclusion.

Cationic-liposomal transfection experiments were carried out using the TransIT®-mRNA Transfection Kit (Minis Bio, WI 53711). Conditions were optimized for keratinocyte and fibroblast transfection according to the manufacturer's recommendations. Transfection of both keratinocytes and fibroblasts was performed in cell culture conditions on a feeder layer of irradiated mouse embryonic fibroblasts.

Flow Cytometry

Flow cytometry was performed using the fluorescent activated cell sorting (FACS®) assay. Flow cytometry was performed on cell subpopulations was performed at the Yale Cancer Center Flow Cytometry Shared Resource, using a FACS® Calibur flow cytometer (Becton-Dickinson, San Jose, Calif.) equipped with 488 nm laser and the standard filter setup. Fluorescence signals were collected on a logarithmic scale. A minimum of ten thousand cells were interrogated for each sample. Analysis of data was performed using FlowJo software (Tree Star, Inc., San Carlos, Calif.). The expression efficiency was calculated as the difference between the geometric mean of fluorescence of the transfectants and control (mock transfected) cells.

Electrophoresis

DNA samples were run in 1% agarose in Tris-acetate buffer, 2 v/cm RNA samples were run in 1% agarose in MOPS-formaldehyde buffer, 2 v/cm, using RNA Millenium marker (Invitrogen) as size standard.

Example 1 mRNA Transfection of Human Fibroblasts

To assess the functionality of mRNA transcripts, transcripts for OCT4, SOX2 (Genbank accession no. NP_003097.1 (protein), NM_003106.2 (mRNA/cDNA)), KLF4 (Genbank: AAH30811.1 (protein), BC030811.1 (mRNA/cDNA)), c-MYC (Genbank: CAA25288.1 (protein), X00676 (mRNA/cDNA)), and NANOG (Genbank: AAP49529.1 (protein), AY230262 (mRNA/cDNA)) were individually transfected into neonatal human foreskin fibroblasts. Protein synthesis was assessed by Western blot analysis. Upon transfection each transcript allowed for significant protein production compared with untransfected control fibroblasts. Sample quantities were standardized by determining pre-lysis cell quantity or by protein quantitation of cell lysates by the bicinchoninic acid (BCA) protein assay.

In all cases protein synthesis was evident above levels of untransfected control samples.

Example 2 mRNA Transfection of Human Keratinocytes

Keratinocytes were transfected with mRNA transcripts coding for reprogramming transcription factors. Initially, keratinocytes were electroporated with OCT4, SOX2, KLF4, and c-MYC mRNA transcripts (day 0). After transfection, cells were grown in keratinocyte medium for 2 days without a feeder cell layer. On day 2, cells were trypsinized and moved to feeder cell layers in multi-well plates with or without 10 mM valproic acid (VPA) supplement.

Transfected keratinocytes began to show evidence of transformation on day 4, at which time small colonies began to form that were particularly abundant in VPA-containing cultures. No colonies were observed in untransfected control cells in either the presence or absence of VPA.

Example 3 siRNA Transfection of Jurkat Cells

Jurkat T cells were electroporated with different amount of FITC labeled siRNA. The condition and the kinetics of siRNA transfection were identical to mRNA transfection. Transfection of Jurkat cells with EGFP mRNA (Clontech) and anti-GFP siRNA (GCAAGCUGACCCUGAAGUU-CAU; SEQ ID NO:1) resulted in 80% inhibition of GFP mRNA expression the day after transfection. No toxicity in siRNA transfection was observed in the interval of 0-15 mkg siRNA/ml.

We claim:

1. A method of re-programming somatic cells comprising transiently transfecting the somatic cells ex vivo with one or more mRNAs in an effective amount to change the somatic cells to a less differentiated state,
   wherein each of the one or more mRNAs are obtained by in vitro transcription of a linear double-stranded DNA template obtained by Polymerase Chain Reaction (PCR),
   the DNA template comprising from the 5' to 3' direction:
   an RNA polymerase promoter on the coding strand of the double-stranded DNA,
   a 5' untranslated region less than 3,000 nucleotides in length and effective for translation of the mRNAs into detectable polypeptides after transfection into the somatic cells,
   an open reading frame that encodes the polypeptide, wherein the polypeptide is one that facilitates dedifferentiation of the cell selected from the group consisting of OCT4, SOX2, NANOG, LIN28, KLF4 and MYC,
   a 3' untranslated region effective for translation of the mRNAs into detectable polypeptides after transfection into a eukaryotic cell, and
   a poly(A) stretch of 50-5,000 nucleotides on the coding strand of the double-stranded DNA,
   wherein the promoter is heterologous to the open reading frame, and
   wherein the DNA template is not contained within a DNA vector and terminates with the 3' end of the poly(A) stretch.

2. The method of claim 1 wherein the somatic cells are transfected with at least two different mRNAs.

3. The method of claim 1 wherein the somatic cells are differentiated cells.

4. The method of claim 1 wherein at least one of the mRNAs is OCT4 mRNA.

5. The method of claim 1 wherein the one or more mRNAs comprise a combination of OCT4, SOX2, NANOG, and LIN28 mRNA.

6. The method of claim 5 wherein the one or more mRNAs comprise a combination of OCT4, SOX2, KLF4 and MYC mRNA.

7. The method of claim 1 further comprising the step of inducing the less differentiated cells to form differentiated cells.

8. The method of claim 7 wherein the differentiated cells are cells from a tissue selected from the group consisting of bone, connective tissue, organ tissue, vascular tissue, skin tissue and nervous tissue or hematopoietic cells.

9. The method of claim 1 further comprising contacting the somatic cells with one or more inhibitory RNAs that reduce expression of an mRNA encoding an allogeneic antigen expressed by the somatic cell.

10. The method of claim 1 wherein the somatic cells are lymphocytes which can be re-programmed into regulatory T cells.

11. The method of claim 6 further comprising growing the transfected cells on a feeder cell layer until small colonies form.

12. The method of claim 1 wherein the somatic cells are fibroblasts or keratinocytes.

13. The method of claim 11 wherein the one or more mRNAs are transiently transfected by multiple administrations staggered minutes, hours, days, or weeks apart.

14. The method of claim 13 wherein the one or more mRNAs comprise modified or artificial nucleotides, or nucleotide analogs.

15. The method of claim 1 further comprising inducing the less differentiated somatic cells to form differentiated cells of a cell type different from the starting somatic cells.

* * * * *

SEQUENCE LISTING

<160> NUMBER OF SEQ ID NOS: 1

<210> SEQ ID NO 1
<211> LENGTH: 22
<212> TYPE: RNA
<213> ORGANISM: Artificial Sequence
<220> FEATURE:
<223> OTHER INFORMATION: chemically synthesized; anti-GFP siRNA

<400> SEQUENCE: 1
gcaagcugac ccugaaguuc au                                              22